United States Patent
Eaton

(10) Patent No.: US 8,922,150 B1
(45) Date of Patent: Dec. 30, 2014

(54) DIFFERENTIAL SERIAL DRIVER

(75) Inventor: Harry A. Eaton, Clarksville, MD (US)

(73) Assignee: The Johns Hopkins University, Baltimore, MD (US)

( * ) Notice: Subject to any disclaimer, the term of this patent is extended or adjusted under 35 U.S.C. 154(b) by 246 days.

(21) Appl. No.: 13/551,781

(22) Filed: Jul. 18, 2012

(51) Int. Cl.
*G05B 19/29* (2006.01)

(52) U.S. Cl.
USPC ............................... 318/601; 375/354; 331/2

(58) Field of Classification Search
USPC ........ 331/2; 307/269; 33/49, 55; 73/862.046; 375/354; 711/105; 318/601
See application file for complete search history.

(56) References Cited

U.S. PATENT DOCUMENTS

| | | | |
|---|---|---|---|
| 5,237,290 A * | 8/1993 | Banu et al. ........................... | 331/2 |
| 5,888,213 A | 3/1999 | Sears et al. | |
| 6,259,326 B1 * | 7/2001 | Dunlop et al. ..................... | 331/2 |
| 6,275,547 B1 * | 8/2001 | Saeki ............................ | 375/354 |
| 6,380,778 B2 | 4/2002 | Uehara et al. | |
| 6,629,776 B2 | 10/2003 | Bell et al. | |
| 6,896,704 B1 | 5/2005 | Higuchi et al. | |
| 6,998,877 B2 | 2/2006 | Lin | |
| 7,078,952 B2 | 7/2006 | Ruat et al. | |
| 7,136,310 B2 | 11/2006 | Kasamsetty | |
| 7,168,748 B2 | 1/2007 | Townsend et al. | |
| 7,193,443 B1 | 3/2007 | Smith et al. | |
| 7,209,720 B2 | 4/2007 | Balasubramaniyan et al. | |
| 7,438,724 B2 | 10/2008 | Sears et al. | |
| 7,466,753 B2 | 12/2008 | Fink et al. | |
| RE40,620 E | 1/2009 | Elder et al. | |
| 7,500,034 B2 | 3/2009 | Eaton | |
| 7,605,557 B2 | 10/2009 | Yourlo et al. | |
| 7,652,386 B2 | 1/2010 | Donelan et al. | |
| 7,675,375 B2 | 3/2010 | Mattisson | |
| 7,679,396 B1 | 3/2010 | Kao | |
| 7,828,857 B2 | 11/2010 | Farnsworth et al. | |
| 2006/0212129 A1 | 9/2006 | Lake et al. | |
| 2008/0200994 A1 | 8/2008 | Colgate et al. | |
| 2008/0205564 A1 * | 8/2008 | Sugawara et al. ............. | 375/354 |
| 2009/0133508 A1 * | 5/2009 | Johansson et al. ........ | 73/862.046 |
| 2010/0016990 A1 | 1/2010 | Kurtz | |
| 2010/0312363 A1 * | 12/2010 | Herr et al. ........................ | 623/39 |
| 2012/0311251 A1 * | 12/2012 | Best et al. ..................... | 711/105 |

FOREIGN PATENT DOCUMENTS

| | | |
|---|---|---|
| WO | 0015157 | 3/2000 |
| WO | 2010120404 | 10/2010 |
| WO | 2011001136 | 1/2011 |
| WO | 2011036473 | 3/2011 |

* cited by examiner

*Primary Examiner* — Rina Duda
*Assistant Examiner* — Bickey Dhakal
(74) *Attorney, Agent, or Firm* — Noah J. Hayward

(57) ABSTRACT

A microcontroller chip includes a serial data transmitter having a serial data output pin and an inverter having an input pin and an output pin, the input pin connected to the serial data output pin of the serial data transmitter, the output pin of the inverter and the output pin of the serial data transmitter forming a differential serial data transmission line.

20 Claims, 4 Drawing Sheets

DIFFERENTIAL SERIAL DRIVER

STATEMENT OF GOVERNMENTAL INTEREST

This invention was made with government support under contract number N66001-06-C-8005 awarded by the Defense Advanced Research Projects Agency (DARPA). The government has certain rights in the invention.

BACKGROUND

Embodiments of the present invention generally relate to a serial driver, and more specifically, relate to a differential serial driver in a small microcontroller.

Microcontrollers are processing chips that may include wide varieties of features, including timing circuits, data processing circuits, and memory circuits. However, as the functionality of the microcontroller has increased, a size of the microcontroller has also necessarily increased to accommodate the additional functionality.

Moreover, microcontrollers located in confined spaces may require a high degree of functionality, but are, at the same time, limited by the space in which the microcontroller is confined. Further, microcontrollers that are small enough to fit within a particular confined space may encounter interference in a serial data line when the microcontroller includes only a serial data transmission line and does not include a differential serial data line.

SUMMARY

According to one example embodiment of the present invention, a microcontroller chip configured to control operation of the motor. The microcontroller chip includes a serial data transmission pin, first and second oscillator connection pins, and an inverter configured to be selectively connected between the first and second data transmission pins according to a transmission or receiving operation. The serial data transmission pin is connected to the first data transmission pin, and the inverter is configured to be connected between the first and second oscillator connection pins during a transmission operation to form a differential serial data transmission line.

According to another embodiment of the present invention, a microcontroller chip includes a serial data transmitter having a serial data output pin, first and second data transmission pins, the serial data output pin connected to the first data transmission pin, and an inverter configured to be selectively connected between the first and second data transmission pins based on a data transmission operation or a data receiving operation, such that the inverter is configured to be connected between the first and second data transmission pins during a data transmission operation to form a differential serial data transmission line.

According to yet another embodiment of the present invention, a human prosthetic limb includes a motor configured to bend a joint of the human prosthetic limb and a microcontroller configured to control operation of the motor, the microcontroller including a serial data transmission pin, first and second data transmission pins, and an inverter configured to be selectively connected between the first and second data transmission pins during a data transmission operation, the serial data transmission pin connected to the first data transmission pin. The serial data transmission pin and the second data transmission pin form a differential serial data transmission line when the inverter is controlled to be connected between the first and second data transmission pins Additional features and advantages are realized. Other embodiments and aspects of the invention are described in detail herein and are considered a part of the claimed invention. For a better understanding of the invention with the advantages and the features, refer to the description and to the drawings.

BRIEF DESCRIPTION OF THE SEVERAL VIEWS OF THE DRAWINGS

The subject matter which is regarded as the invention is particularly pointed out and distinctly claimed in the claims at the conclusion of the specification. The forgoing and other features, and advantages of the invention are apparent from the following detailed description taken in conjunction with the accompanying drawings in which:

DETAILED DESCRIPTION

Figure 1:
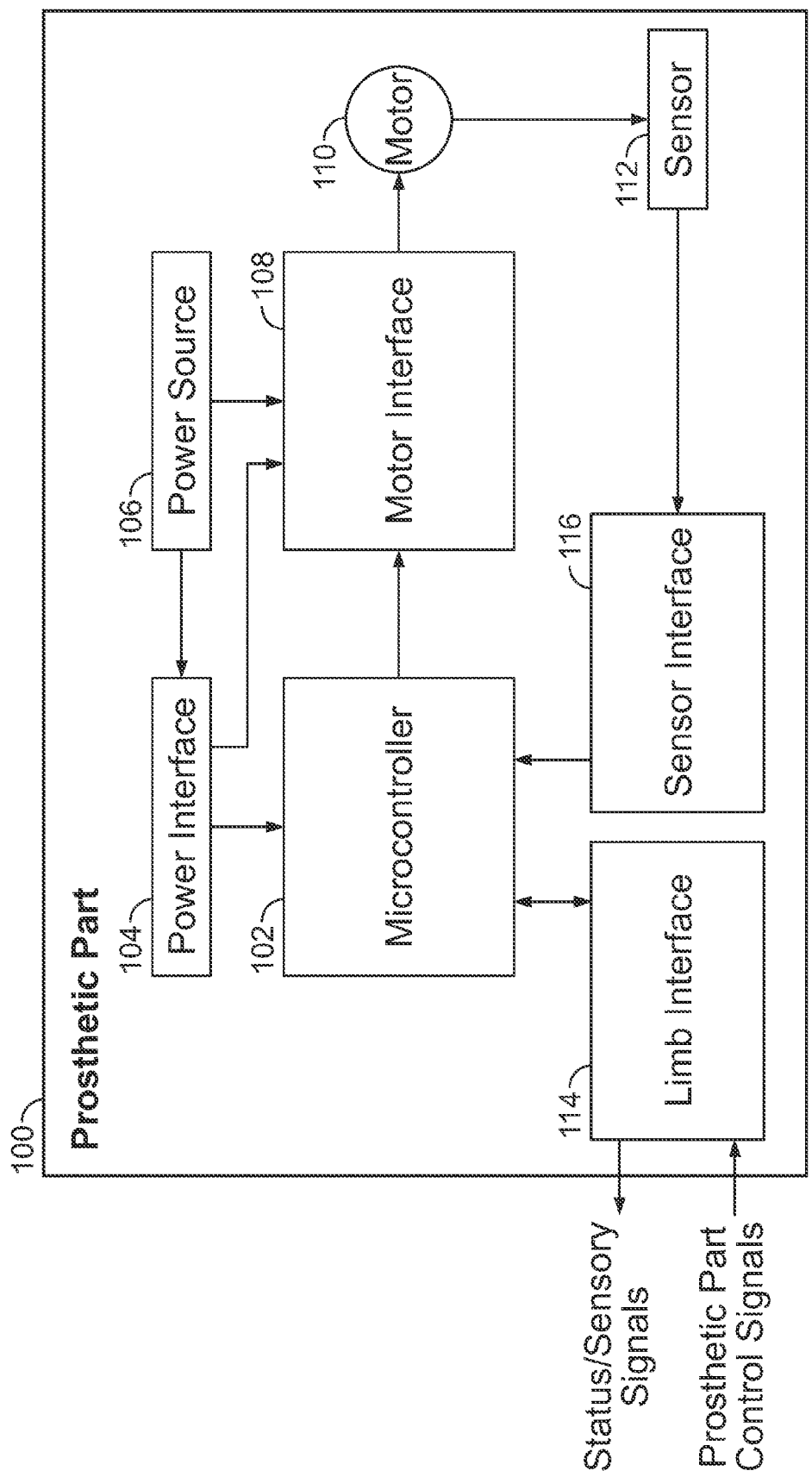
FIG. 1 illustrates a prosthetic part system according to an embodiment of the invention.

With reference now to FIG. 1, a prosthetic part system 100 according to an embodiment of the invention includes a microcontroller 102, motor interface 108, and motor 110. The prosthetic part system 100 further includes a power interface 104 and power source 106 configured to control power supplied to the microcontroller 102 and the motor interface 108. The power source 106 may be, for example, a battery, and the power interface 104 may be a power converter configured to convert a power level or a type of power, such as alternating current (AC)-to-direct current (DC) or DC-to-AC. The prosthetic part system 100 further includes a limb interface 114 configured to receive prosthetic part control signals from an external prosthetic part controller (not shown) and to transmit status data and sensory data to the external prosthetic part controller. The prosthetic part system 100 further includes one or more sensors 112 and a sensor interface 116 to transmit data from the sensors 112 to the microcontroller 102.

In operation, the microcontroller 102 receives instructions from an external prosthetic part controller via the limb interface 114 to control the motor 110. The external prosthetic part controller may be located externally to the prosthetic part 100 or inside the prosthetic part at a location separated from the microcontroller 102. In one embodiment, the microcontroller 102 is a single chip within circuit. In one embodiment, the motor 110 is a brushless DC motor, or an AC synchronous motor driven with a 3-phase AC signal. The phases may be generated by applying pulse-width modulated (PWM) signals on three half-bridges. The microcontroller 102 transmits control signals, such as the PWM signals to the motor interface 108, and the motor interface 108 transmits control signals to the motor 110.

In one embodiment, the motor interface 108 includes one or more of a gate driver and a half bridge. The microcontroller 102 may include a pulse-width modulator to generate pulse-width modulated signals to control gates of the half bridge circuit. The voltage supplied by the power source 106 and/or the power interface 104 is transmitted to the motor 110 according to the pulse-width modulated signals output from the microcontroller 102. For example, in one embodiment the power source 106 outputs a DC power signal, and the DC power signal is pulse-width modulated to supply modulated AC control signals to the motor 110.

The sensor 112 detects a characteristic of the motor 110, such as a position or rotation speed of the motor 110 and outputs a sensor signal to the sensor interface 116. The sensor interface 116 transmits the sensor signal to the microcontroller 102. The sensor interface 116 may include wiring and one or more conditioning, filter, or voltage or current conversion or amplification circuits. The microcontroller 102 may adjust output control signals to the motor based on the sensor signals, and may output status signals to an external prosthetic part controller based on the sensor signals. In addition, the microcontroller 102 may receive sensory inputs such as temperature, pressure, or pain inputs from sensors in the prosthetic part system 100 and may transmit the sensory signals to the prosthetic part controller.

In one embodiment of the invention, the prosthetic part system 100 is a prosthetic limb, such as a prosthetic arm, prosthetic hand, prosthetic finger, prosthetic leg, prosthetic foot, or prosthetic toe. In particular, in one embodiment of the present invention, the prosthetic part system 100 is a prosthetic hand, and the microcontroller 102, power source 106, motor 110, sensor 112 and other components of the prosthetic part system 100 are all located within the prosthetic hand. In addition, one or more of the microcontroller 102, motor interface 108, and motor 110 may be located within a finger of the prosthetic part 100.

Since the power source 106 and power interface 104 are located in close proximity to data transmission lines, such as transmission lines between the microcontroller 102 and the limb interface 114 and the sensor interface 116, the power source 106 and corresponding power transmission wiring may generate noise or interference, and the prosthetic part system 100 may be configured to reduce the effects of the noise or interference on the data lines. In particular, the microcontroller 102 may be configured such that one or more of the limb interface 114 data line, the sensor interface 116 data line or any other data line is a differential serial transmission/receiving data line.

Figures 2A, 2B:
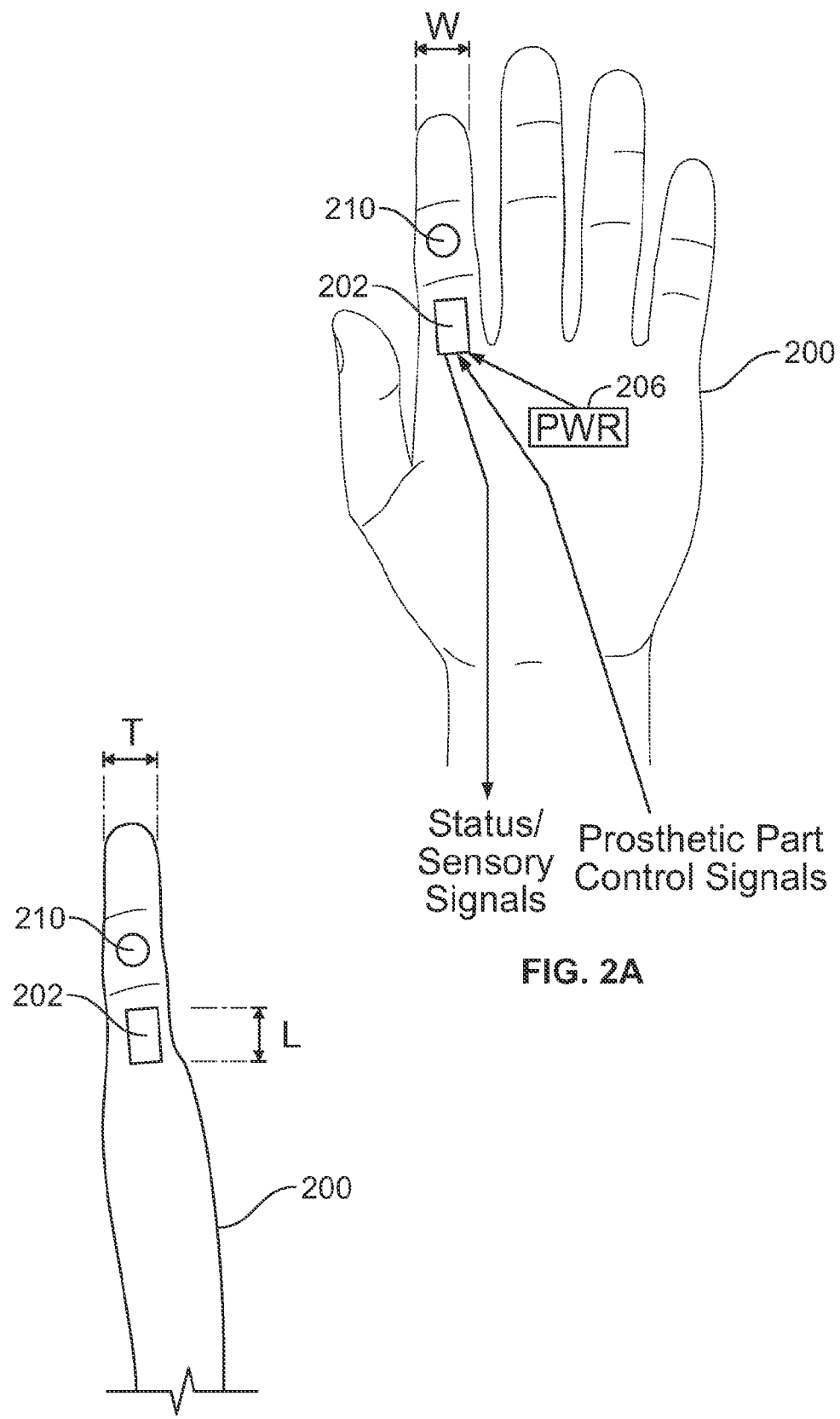
FIGS. 2A and 2B illustrate a prosthetic hand according to an embodiment of the invention.

FIGS. 2A and 2B illustrate a prosthetic hand 200 according to an embodiment of the invention. In FIG. 2A, the prosthetic hand 200 includes a microcontroller 202, a motor 210 and a power source 206. The microcontroller 202, the motor 210 and the power source may correspond to the microcontroller 102, the motor 110 and the power source 206 of FIG. 1. Although all the components illustrated in FIG. 1 are not illustrated in FIG. 2 for purposes of clarity in illustration, the prosthetic hand 200 may correspond to the prosthetic part system 100 of FIG. 1 and all the components illustrated in the prosthetic part system 100 of FIG. 1 may be located within the prosthetic hand 200 of FIG. 2. In addition, the prosthetic part system 100 and prosthetic hand 200 are not limited to the parts illustrated in FIGS. 1 and 2, but additional parts may be provided for additional functionality, limited by the specifications of the prosthetic part system 100 and space available within the prosthetic part system 100 or prosthetic hand 200.

The motor 210 may be located in a joint of a finger of the prosthetic hand 200 to bend the joint. The microcontroller 202 may also be located in the finger. Since the microcontroller 202 is located within the finger, space for the microcontroller 202 and supporting circuitry such as sensors, interface circuits, circuit board substrates and wiring is limited to a width W, a length L, and a thickness T. In one embodiment, W is about 0.6 cm or less, L is about 1 cm or less, and T is about 0.6 mm or less. In one embodiment, the dimensions of the microcontroller 202 are about 4-6 mm in width W, about 4-6 mm in length L, and about 0.5-0.8 mm in thickness T.

In embodiments of the present disclosure, the data outputs, such as the sensory and status signals output from the microcontroller 202 are in the vicinity of the power source 206 and the power lines running from the power source 206 to the microcontroller 202 and the motor 210. In particular, due to the space constraints within the prosthetic part system 100 and the prosthetic hand 200, the data lines output from the microcontroller 102 and 202 are within the same casing (i.e. the shell of the hand) as the power source 106 and 206 and the power lines, and may be within about 1 cm of the power source 106 and 206 or the power lines.

In embodiments of the present invention, the microcontroller 102 or 202 may not have an output dedicated to a differential serial communication signal, which provides improved data stability relative to a non-differential serial communication signal. In other words, due to space, cost or availability factors, the microcontroller 102 or 202 may include only a non-differential serial input pin and serial output pin. For example, in one embodiment, the microcontroller 102 or 202 may be a SILICON LABS C8051F411, '12 or '13 microcontroller.

Figure 4:
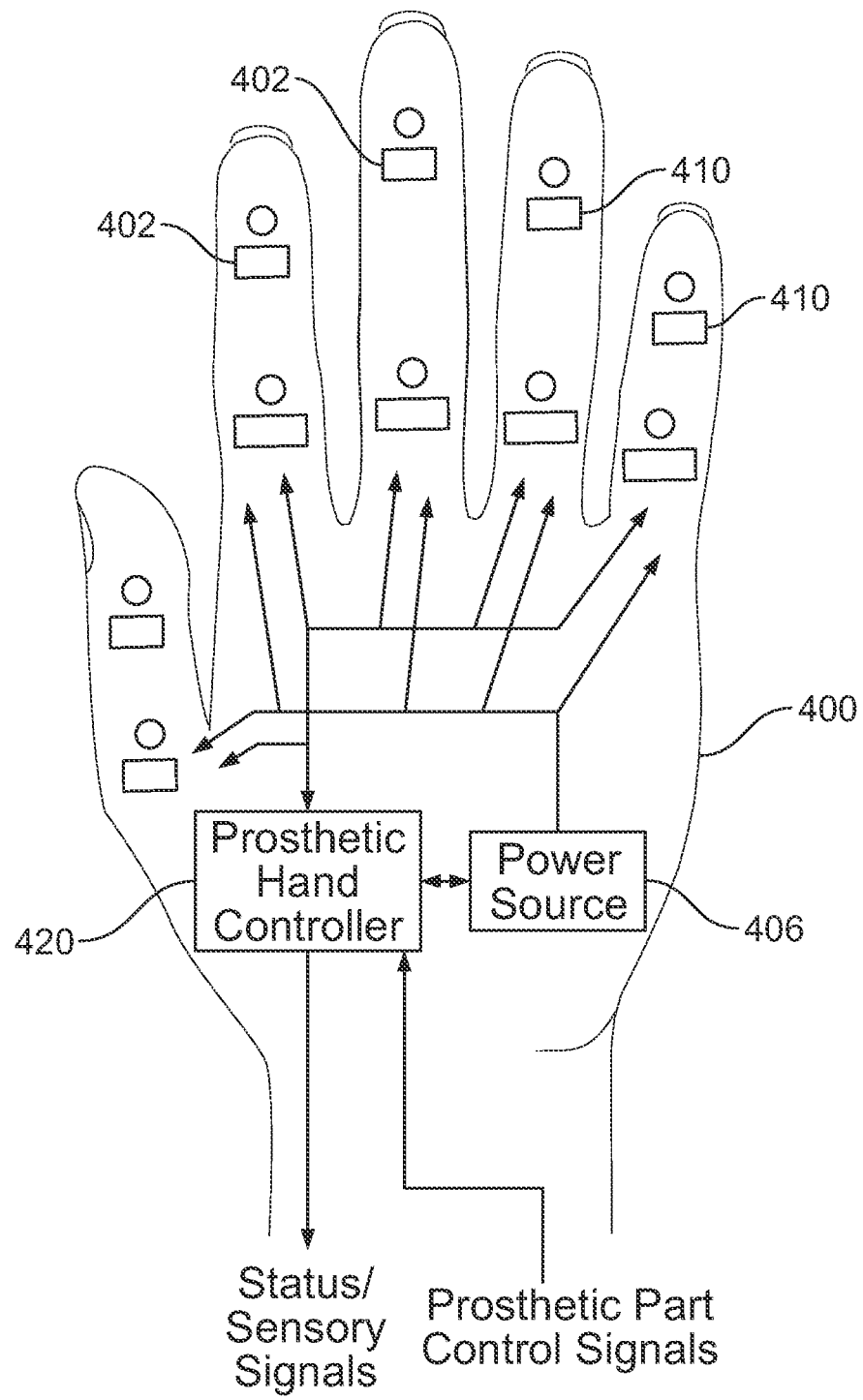
FIG. 4 illustrates a prosthetic hand according to an embodiment of the invention.

Although one microcontroller chip 202 and one motor 210 are illustrated in FIGS. 2A and 2B for purposes of clarity, embodiments of the present disclosure encompass any number of microcontroller chips and motors. FIG. 4 illustrates an example of a prosthetic hand 400 including a separate microcontroller chip 402 and motor 410 for each joint of each finger in the hand. The power source 406 may provide power to each microcontroller chip 402 and motor 410. In addition, a prosthetic hand controller 420 may be provided to control each of the microcontroller chips 402.

In the embodiment illustrated in FIG. 4, the microcontroller chip 402, power source 406 and motor 410 may correspond to the microcontroller chip 202, power source 206 and motor 210 of FIG. 2. In some embodiments, each microcontroller chip 402 includes its own power interface, such as the power interface 104 illustrated in FIG. 1, such that each microcontroller chip 402 may provide a separate level of power to a corresponding motor 410.

Although embodiments illustrated in FIGS. 2A, 2B and 4 illustrate a prosthetic human hand, embodiments of the present invention encompass any prosthetic human limb, any prosthetic limb of any animal, any limb of a robot or other mechanical device, or any other outer casing having stored therein a microcontroller chip and a power source, power interface, or power wiring in close proximity to data lines of the microcontroller chip.

Figure 3:
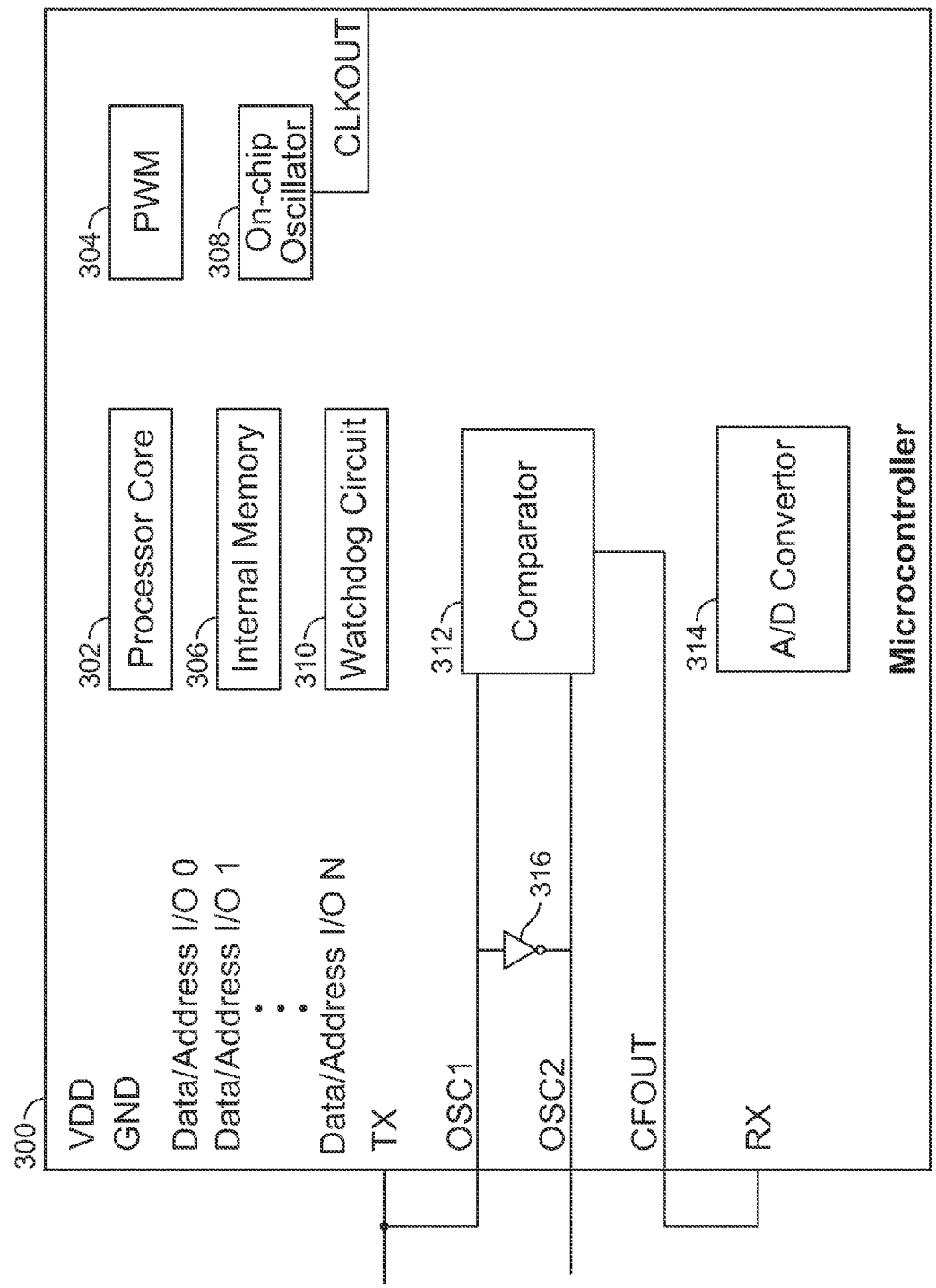
FIG. 3 illustrates a microcontroller chip according to an embodiment of the invention.

In an embodiment of the present disclosure, the microcontroller 102, 202 or 402 does not use an external oscillator, and wiring and internal programming are provided to generate a differential serial input and output signal. Referring to FIG. 3, a microcontroller chip 300 may include a core processor 302, pulse-width modulator 304, internal memory 306, on-chip oscillator 308, watchdog circuit 310, comparator 312, and analog-to-digital converter 314 and inverter. The microcontroller chip 300 further includes at least a power pin VDD, a ground pin GND, data/address pins I/O 0 to I/O N, a serial data output pin TX, a serial data input pin RX, external oscillator connection pins OSC1 and OSC2, and a clock output pin CLKOUT. The oscillator connection pins OSC1 and OSC2 are connected to the inverter 316, so that when an oscillation crystal external to the microcontroller chip 300 is connected to the oscillator connection pins OSC1 and OSC2, the oscillation crystal oscillates at a predetermined frequency. The microcontroller chip 300 of FIG. 3 may correspond to any one of the microcontroller chips 102, 202, 402 and 420 of FIGS. 1, 2A, 2B and 4.

The on-chip oscillator 308 may be configured to provide a clock signal to internal and external circuits. The watchdog circuit 310 may be configured to detect predetermined errors or failures, and may initiate a reset of the microcontroller chip 300 when the predetermined error or failure is detected. The internal memory 306 may include data storage for storing addresses, operand data and may be structured as registers, stacks or in any other data structure. The A/D converter 314 is configured to receive analog signals, such as sensor input signals received via the data pins I/O 0 to I/O N and to convert the analog signals to digital signals. The digital sensor signals may then be stored in internal memory 306 or transmitted to the processor core 302 for processing. The pulse-width modulator 304 is configured to output pulse-width modulated signals to control a motor, such as the motor 110 of FIG. 1 or the motor 210 of FIG. 2. The processor core 302 may control the pulse-width modulator 304 based on sensor signals and prosthetic part control signals received via the data I/O pins 0 to N.

In one embodiment, the microcontroller chip 300 may be configured such that one or more of the sensor data and prosthetic part control data may is received at the oscillator pins OSC1 and OSC 2. The oscillator pins OSC1 and OSC2 may be internally connected or programmed to be transmitted to the comparator 312, thereby providing a differential serial input to the microcontroller chip 300. The output from the comparator may be output via a comparator output pin CFOUT, and the comparator output pin CFOUT may be electrically connected via wiring to the serial data input pin RX. Accordingly, even in a processor having no dedicated serial input pins, serial communication may be provided by wiring the microcontroller chip 300 to receive serial input wires at two pins connected to a comparator 312, and by connecting a comparator output pin CFOUT to a serial data input pin RX. While in the embodiment illustrated in FIG. 3 the comparator output is hard-wired to the serial data input pin RX via a wire external to the microcontroller chip 300, in other embodiments, the microcontroller chip 300 may include internal wiring or programming to provide an output of the comparator 312 to a serial data input location, such as a serial data input buffer, address, storage in internal memory 306 or connection to the processor core 302.

In addition to the differential serial input connections, the serial data output pin TX may be connected via an external wire to the oscillator pin OSC1, resulting in an inverted TX signals at OSC2, and a differential serial output signal between the serial data output pin TX and the oscillator pin OSC2. As a result, a serial data output may be provided without requiring external circuitry, such as an inverter external to the microcontroller chip 300. Instead, pins intended to control an oscillator may be re-wired to generate a differential serial output on a microcontroller chip 300 having no dedicated differential serial input or output pins, where dedicated differential serial input and output pins are defined as pins that are pre-designated or pre-configured by a microcontroller chip manufacturer as corresponding to differential serial communication, or pins being programmable to provide differential serial communication.

In one embodiment, software is used to disconnect the inverter 316 from the oscillator pins OSC1 and OSC2 during reception of data signals and to connect the inverter 316 to the oscillator pins OSC1 and OSC2 during a data transmission operation. In such an embodiment, the microcontroller chip 300 is configured as a half-duplex communications path where it is not possible to simultaneously transmit and receive differential data communications. Accordingly, the compara-tor is not connected to the pins of the inverter 316, but to the oscillator pins OSC1 and OSC2.

In one embodiment, a limb chip, such as the prosthetic hand controller 420 of FIG. 4, is a "bus master" that controls access to the bus for multiple motor controllers and sensors on the same communications bus. Upon receipt of a valid command, software of the limb controller re-configures the pins of the microcontroller chip 300 for data transmission and sends a response message, after which the software returns the configuration of the microcontroller chip 300 to the listening mode.

In other words, while FIG. 3 illustrates the inverter 316 connected between the oscillator pins OSC1 and OSC2, in one embodiment the inverter 316 is connected only during a transmission operation, and is disconnected during a receiving operation. In another embodiment, the microcontroller chip 300 is configured to be a full-duplex system having comparator pins on a separate receive-only pair of pins from the oscillator pins OSC1 and OSC2.

In embodiments of the present invention, a microcontroller chip having no dedicated differential serial communication pins and having no capability to internally program pins to provide differential serial communication may be re-wired to provide differential serial communication. In one embodiment, external oscillator connection pins that are connected internally to an inverter may be wired externally to provide differential serial communication. In particular, an oscillator pin connected to an input of the inverter may be connected to the serial data output pin, and the serial data output pin and the output of the inverter may form a differential serial output.

In addition, serial data communication lines may be connected to a comparator, and the comparator may be connected to a non-differential serial data input pin of the microcontroller. In one embodiment, the microcontroller is internally programmable to connect the oscillator pins to a comparator internal to the microcontroller, and a comparator output pin may be wired to be connected to the non-differential serial data input pin.

In one embodiment of the present disclosure, the microcontroller may be limited to a predetermined size, such as a length of about 4-6 mm, a width of about 4-6 mm, and a thickness of about 0.5-0.8 mm. For example, the microcontroller may be configured to be located within a human prosthetic limb, such as a finger of a prosthetic human hand. Accordingly, the differential serial communication lines may provide data reliability in a confined space which may include interference sources, such as a power source and a motor.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one more other features, integers, steps, operations, element components, and/or groups thereof.

The description of the various example embodiments of the present invention has been herein presented for purposes of illustration and description, but is not intended to be exhaustive or limited to the invention in the form disclosed. Many modifications and variations will be apparent to those of ordinary skill in the art without departing from the scope and spirit of the invention. The embodiments have been chosen and described in order to best explain the principles of the invention and the practical application, and to enable others of ordinary skill in the art to understand the invention for various embodiments with various modifications as are suited to the particular use contemplated While the preferred embodiment(s) to the invention have been described, it will be understood that those skilled in the art, both now and in the future, may make various improvements and enhancements which fall within the scope of the claims which follow.

What is claimed is:

1. A system for controlling a motor, comprising:
a microcontroller chip configured to control operation of the motor, the microcontroller chip including a serial data transmission pin, first and second data transmission pins, and an inverter configured to be selectively connected between the first and second data transmission pins according to a transmission or a receiving operation, the serial data transmission pin connected to the first data transmission pin,
wherein the inverter is configured to be connected between the first and second data transmission pins during a transmission operation to form a differential serial data transmission line.

2. The system of claim 1, wherein the microcontroller chip is configured to be positioned within a prosthetic limb.

3. The system of claim 1, wherein the motor is configured to bend a joint of a finger of a prosthetic hand, and both the motor and the microcontroller chip are configured to be positioned within the finger of the prosthetic hand.

4. The system of claim 1, wherein the microcontroller has a length from about 4 millimeters (mm) through about 6 mm, a width from about 4 mm through about 6 mm, and a thickness less than about 1 mm.

5. The system of claim 1, wherein the microcontroller chip includes a comparator to compare signals on the first and second data transmission pins, and
wherein an output pin of the comparator is connected to a serial data receiving pin.

6. The system of claim 1, further comprising:
a power source; and
a human prosthetic limb part,
wherein the motor, the microcontroller chip, and the power source are located within the human prosthetic limb part.

7. The system of claim 1, wherein the serial data transmission pin is connected to the input pin of the inverter via wiring external to the microcontroller.

8. The system of claim 6, wherein the differential serial data line is configured to communicate with a prosthetic limb controller external to the prosthetic limb part.

9. The system of claim 6, wherein the differential serial data line is configured to communicate with a prosthetic limb controller located inside the prosthetic limb part.

10. A microcontroller chip, comprising:
a serial data transmitter having a serial data output pin;
first and second data transmission pins, the serial data output pin connected to the first data transmission pin; and
an inverter configured to be selectively connected between the first and second data transmission pins based on a data transmission operation or a data receiving operation, such that the inverter is configured to be connected between the first and second data transmission pins during a data transmission operation to form a differential serial data transmission line.

11. The microcontroller chip of claim 10, further comprising:
a comparator configured to compare signals on the first and second data transmission pins,
wherein an output pin of the comparator is connected to a serial data receiving pin.

12. The microcontroller chip of claim 10, wherein the microcontroller chip has a length from about 4 mm through about 6 mm, a width from about 4 mm through about 6 mm, and a thickness less than about 1 mm.

13. The microcontroller chip of claim 10, wherein the serial data output pin is connected to the input pin of the inverter via external wiring.

14. The microcontroller chip of claim 10, further comprising:
memory to store control software; and
a processor core to execute the control software to connect the inverter between the first and second data transmission pins during a data transmission operation and to disconnect the inverter from between the first and second data transmission pins during a data receiving operation.

15. The microcontroller chip of claim 11, further comprising:
a plurality of additional data transmission pins configured to transmit sensor data to the microcontroller chip and motor control signals to a motor;
an analog-to-digital converter configured to convert the sensor data;
a pulse-width modulator configured to generate the motor control signals;
a processor core configured to process the sensor data from the analog-to-digital converter and to control the pulse-width modulator to generate the motor control signals based on the sensor data; and
memory configured to store at least one of commands and operand data to control processing operations of the processor.

16. A human prosthetic limb, comprising:
a motor configured to bend a joint of the human prosthetic limb; and
a microcontroller configured to control operation of the motor, the microcontroller including a serial data transmission pin, first and second data transmission pins, and an inverter configured to be selectively connected between the first and second data transmission pins during a data transmission operation, the serial data transmission pin connected to the first data transmission pin,
wherein the serial data transmission pin and the second data transmission pin form a differential serial data transmission line when the inverter is controlled to be connected between the first and second data transmission pins.

17. The human prosthetic limb of claim 16, wherein the human prosthetic limb is a human prosthetic hand, and
wherein the motor and the microcontroller are located within a finger of the human prosthetic hand.

18. The human prosthetic limb of claim 16, wherein the microcontroller has a length from about 4 mm through about 6 mm, a width from about 4 mm through about 6 mm, and a thickness less than about 1 mm.

19. The human prosthetic limb of claim 16, wherein the microcontroller includes a comparator to compare signals on the first and second data transmission pins, and
wherein an output pin of the comparator is connected to a serial data receiving pin.

20. The human prosthetic limb of claim 16, further comprising:
a power source located within the human prosthetic limb.

* * * * *